United States Patent [19]

Takatsuna et al.

[11] Patent Number: 5,145,979
[45] Date of Patent: Sep. 8, 1992

[54] PROCESSES FOR THE PREPARATION OF γ-METHACRYLOXYPROPYLSILANE COMPOUNDS

[75] Inventors: Kazutoshi Takatsuna; Masaaki Ishii, both of Yokohama; Hideaki Ogawa, Chigasaki; Akihito Shinohara, Kamifukuoka; Kouji Shiozawa, Saitama; Yoshiharu Okumura, Shinjuku; Masako Ishikawa, Saitama, all of Japan

[73] Assignee: Tonen Corporation, Tokyo, Japan

[21] Appl. No.: 748,557

[22] Filed: Aug. 22, 1991

[30] Foreign Application Priority Data

Aug. 23, 1990 [JP] Japan ................................. 2-222151
Sep. 19, 1990 [JP] Japan ................................. 2-249283
Sep. 19, 1990 [JP] Japan ................................. 2-249284

[51] Int. Cl.$^5$ ............................ C07F 7/08; C07F 7/18
[52] U.S. Cl. .................................................. 556/440
[58] Field of Search ......................................... 556/440

[56] References Cited

U.S. PATENT DOCUMENTS

| | | | |
|---|---|---|---|
| 4,276,426 | 6/1981 | Lindner et al. | 556/479 |
| 4,614,812 | 9/1986 | Schilling | 556/440 X |
| 4,709,067 | 11/1987 | Chu et al. | 556/440 |
| 4,780,555 | 10/1988 | Bank | 556/440 |
| 4,946,977 | 8/1990 | Bernhardt et al. | 556/440 |

FOREIGN PATENT DOCUMENTS 0247501 12/1987 European Pat. Off. .
0277023 8/1988 European Pat. Off. .

*Primary Examiner*—Paul F. Shaver
*Attorney, Agent, or Firm*—Wenderoth, Lind & Ponack

[57] ABSTRACT

There are provided processes for the preparation of γ-methacryloxypropylsilane compounds which comprise carrying out the reaction of allyl methacrylate with a hydrosilane compound in the presence of a platinum catalyst, while allowing at least one of a hindered phenol compound and an aromatic amine compound to coexist in the reaction system with an alkylamine compound or an amide compound, or with a gas containing molecular oxygen, or with a phenol compound having an aminoalkylene group. By using these processes as provided, gelation of the reaction mixture in the reaction system and during the course of purification thereof by distillation can effectively be avoided, and the desired γ-methacryloxypropylsilane compounds can be obtained in good yield.

6 Claims, No Drawings

PROCESSES FOR THE PREPARATION OF γ-METHACRYLOXYPROPYLSILANE COMPOUNDS

FIELD OF THE INVENTION

This invention relates to processes for the preparation of γ-methacryloxypropylsilane compounds, and more particularly to a process for preparing γ-methacryloxypropylsilane compounds, wherein allyl methacrylate is allowed to react with a hydrosilane compound in one stage to obtain the γ-methacryloxypropylsilane compounds in high yield without causing gelation of reaction mixture in the reaction system and during the course of purification by distillation.

BACKGROUND OF THE INVENTION

γ-methacryloxypropylsilane compounds such as γ-methacryloxypropyltrimethoxysilane, and γ-methacryloxypropyltriethoxysilane have a hydrolyzable group reacting with inorganic substances as well as an organic functional group in a molecule, and are widely used as coupling agents.

As a process for the preparation of such γ-methacryloxypropylsilane compounds as mentioned above, it is known to allow to react, for example, allyl methacrylate with trichlorosilane in the presence of a platinum catalyst and isolate γ-methacryloxypropyltrialkoxysilane as a product from the reaction mixture after treatment with alcohol.

In this process, however, corrosive hydrogen chloride is formed during the γ-methacryloxypropylalkoxysilane synthesis. This process, therefore, involves such disadvantages that the removal of the hydrogen chloride is indispensable for carrying out the process and the chlorine content in the end product increases.

As a process for the preparation of γ-methacryloxypropylsilane compounds, in which no removal of hydrogen chloride is required and there is no fear of increasing the chlorine content in the end product, it is known to allow allyl methacrylate to react with a hydrosilane compound such as trialkoxysilane or the like in one stage (hydrosilyl reaction) in the presence of a platinum based catalyst, and purify the reaction mixture by distillation.

In the process as mentioned above, however, there was involved such disadvantages that gelation of the reaction mixture or product is caused by polymerization of the material, i.e. an allyl methacrylate during the course of reaction, or polymerization of the reaction product, i.e. a γ-methacryloxypropylsilane compound during the course of purification thereof. By virtue of such gelation as will occur in the reaction system and during the purification, the yield of the γ-methacryloxypropylsilane compound will decrease and it becomes difficult to isolate efficiently the γ-methacryloxypropylsilane compound from the reaction mixture containing the gel, because the gel once formed is sparingly soluble in the solvent and difficult to remove.

Under such circumstances, there has been proposed a process intended to inhibit the formation of the gel as aforesaid, wherein a hydrosilane compound and allyl methacrylate are added simultaneously to a toluene solution containing 2,5-di-t-butylhydroquinone as a polymerization inhibitor and a chloroplatinic acid solution as a catalyst (see U.S. Pat. No. 3,258,477). However, this process was economically disadvantageous in that large amounts of toluene as the solvent must be used.

Furthermore, there have heretofore been proposed various processes aiming at preventing the gel formation by using diverse polymerization inhibitors, for example, phenol compounds such as hindered phenol, aromatic amine compounds such as diphenylenediamine, or aromatic sulfur compounds such as phenothiazine (see, for example, Japanese Patent Laid-Open Nos. 283983/1987 and 188689/1988). However, no sufficient prevention of the gel formation in the reaction system and during the course of purification of the reaction mixture by distillation was achieved yet, and there is a strong and growing demand for a process capable of preventing effectively the gel formation as mentioned above.

OBJECT OF THE INVENTION

The present invention is intended to solve such problems associated with the prior art as mentioned above, and an object of the invention is to provide processes for the preparation of γ-methacryloxypropylsilane compounds by reaction of allyl methacrylate with a hydrosilane compound in the presence of a platinum catalyst in one stage, wherein gelation of the reaction mixture in the reaction system and during the course of purification thereof by distillation can effectively prevented, thereby obtaining the end γ-methacryloxypropylsilane compound in good yield and at a moderate cost.

SUMMARY OF THE INVENTION

The first process for the preparation of γ-methacryloxypropylsilane compounds of the present invention is characterized by carrying out the reaction of allyl methacrylate with a hydrosilane compound in the presence of a platinum catalyst, while allowing at least one compound selected from the group consisting of a hindered phenol compound and an aromatic amine compound to coexist in the reaction system with an alkylamine compound.

The second process for the preparation of γ-methacryloxypropylsilane compounds of the invention is characterized by carrying out the reaction of allyl methacrylate with a hydrosilane compound in the presence of a platinum catalyst, while allowing at least one compound selected from the group consisting of a hindered phenol compound and an aromatic amine compound to coexist in the reaction system with an amide compound.

The third process for the preparation of γ-methacryloxypropylsilane compounds of the invention is characterized by carrying out the reaction of allyl methacrylate with a hydrosilane compound in the presence of a platinum catalyst, while allowing at least one compound selected from the group consisting of a hindered phenol compound and an aromatic amine compound to exist in the reaction system and blowing a gas containing molecular oxygen into the reaction mixture.

The fourth process for the preparation of γ-methacryloxypropylsilane compounds of the invention is characterized by carrying out the reaction of allyl methacrylate with a hydrosilane compound in the presence of a platinum catalyst, while allowing a phenol compound having an aminoalkylene group to exist in the reaction system.

DETAILED DESCRIPTION OF THE INVENTION

The processes for the preparation of γ-methacryloxypropylsilane compounds of the present invention are described below in detail.

The first to fourth processes for the preparation of γ-methacryloxypropylsilane compounds of the invention comprise carrying out the reaction of allyl methacrylate with a hydrosilane compound in the presence of a platinum catalyst, while allowing a specific polymerization inhibitor or a specific combination thereof to exist in the reaction system.

By the term hydrosilane compound as used herein is meant a compound having at least one Si—H bond, for example, the compound represented by the general formula [I], [II] or [III] as mentioned below.

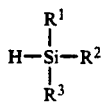

[I]

wherein $R^1$, $R^2$ and $R^3$, which may be the same or different, are each alkyl or alkoxy.

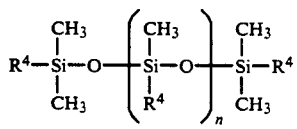

[II]

wherein $R^4$ is hydrogen or methyl, at least one of $R^4$ is hydrogen, and n is an integer of from 0 to 300.

[III]

wherein m is an integer of from 3 to 10.

Concrete examples of the hydrosilane compound as represented by the above formula [I], [II] or [III] are triethoxysilane, trimethoxysilane, trimethylsilane, triethylsilane, tripropoxysilane, tributoxysilane, methyldimethoxysilane, ethyldimethoxysilane, methyldiethoxysilane, dimethylmethoxysilane, trioctyloxysilane, methyldioctyloxysilane, dimethyloctyloxysilane, 1,1,3,3-tetramethyldisiloxane, pentamethyldisiloxane, α,ω-dihydropolysiloxane, polysiloxane having Si—H bond between the molecular chains, 1,3,5,7-tetramethylcyclotetrasiloxane and 1,3,5,7,9-pentamethylcyclopentasiloxane.

In the process for the preparation of γ-methacryloxypropylsilane compounds of the present invention, allyl methacrylate and such a hydrosilane compound as exemplified above are used in the proportion in terms of the (allyl methacrylate/hydrosilyl group of the hydrosilane compound) molar ratio of usually 0.66/1.5, preferably 0.83/1.2.

In the present invention, any platinum catalysts so far used in the hydrosilylation reaction may be used as the catalyst. However, preferable platinum catalysts in the invention include chloroplatinic acid, dichlorobis(acetonitrile)platinum (II), dichlorodiethylene platinum (II), dichloro(1,5-cyclooctadiene)platinum (II), platinum vinylsiloxane complex, and supported platinum such as platinum supported on activated carbon or platinum supported on alumina.

The above-exemplified platinum catalyst is used in an amount, based on the allyl methacrylate used, of usually from $1 \times 10^{-7}$ to $1 \times 10^{-3}$ mole, preferably from $1 \times 10^{-6}$ to $1 \times 10^{-4}$ mole.

In the first process for the preparation of γ-methacryloxypropylsilane compounds of the invention, the reaction of the above-mentioned hydrosilane compound with allyl methacrylate is carried out in the presence of the above-mentioned platinum catalyst, while allowing at least one compound selected from the group consisting of a hindered phenol compound and an aromatic amine compound to coexist in the reaction system with an alkylamine compound.

The hindered phenol compound used in the first process of the invention has at least one bulky substituent at the position near the hydroxy group in the aromatic ring, and may be any hindered phenol compounds so far used as a polymerization inhibitor in the hydrosilylation reaction.

Such hindered phenol compounds as mentioned above include concretely those as listed below, showing their respective structural formulas in which tBu represents $-C(CH_3)_3$(t-butyl).

(1) 2,6-di-t-butyl-p-cresol (BHT)

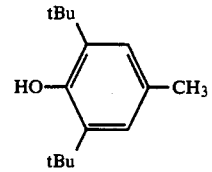

(2) 2,6-di-t-butylphenol

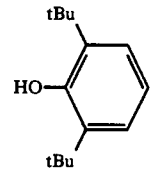

(3) 2-methyl-6-t-butyl-p-cresol (MBPC)

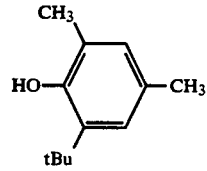

(4) 2-t-butyl-4-methoxyphenol

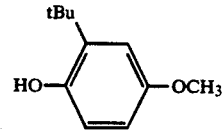

(5) 2,5-di-t-butylhydroquinone
(trade name: Antage DBH, a product of Kawaguchi Kagaku K.K.)

-continued

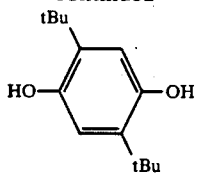

(6) n-octadecyl-3-(3',5'-di-t-butyl-4'-hydroxyphenyl)-propionate
(trade name: Irganox ® 1076, a product of Ciba-Geigy)

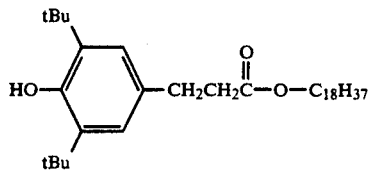

(7) 4,4'-methylene-bis(2,6-di-t-butylphenol)
(trade name: Ethanox ® 702, a product of Ethyl Co.)

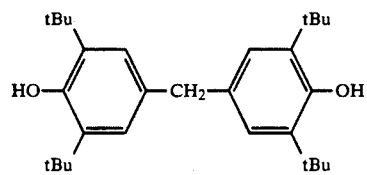

(8) 2,2'-methylene-bis(4-methyl-6-t-butylphenol)

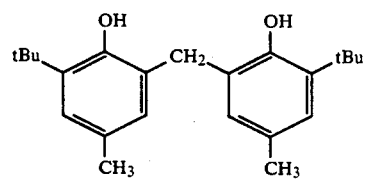

(9) 2,2'ethylidene-bis(4,6-di-t-butylphenol)
(trade name: Isonox ® 129, a product of Schenectady Co.)

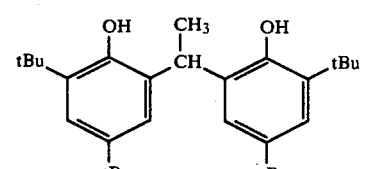

(10) 2,2'-butylidene-bis(6-t-butyl-4-methylphenol)
(trade name: Sumilizer ® BBP, a product of Sumitomo Kagaku Kogyo K.K.)

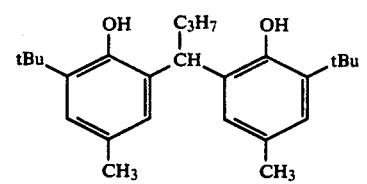

(11) 4,4'-butylidene-bis(2-t-butyl-5-methylphenol)

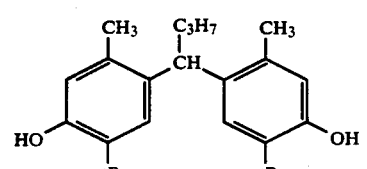

-continued

(12) 2-t-butyl-6-(3'-t-butyl-5'-methyl-2'-hydroxybenzyl)-4-methylphenyl acrylate
(trade name: Sumilizer ® GM, a product of Sumitomo Kagaku Kogyo K.K.)

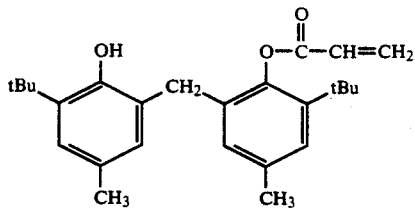

(13) tetrakis(methylene-3-(3',5'-di-t-butyl-4'-hydroxyphenol)propionate)methane
(trade name: Irganox ® 1010, a product of Ciba-Geigy)

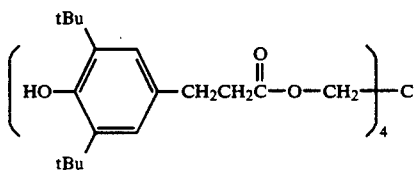

(14) (mono, di, tri)α-methylbenzylphenol

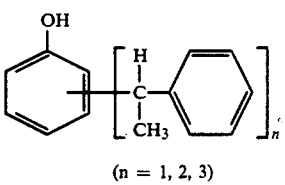

(n = 1, 2, 3)

The hindered phenol compounds as exemplified above are used in an amount, based on the allyl methacrylate used, of from 1 ppm to 20% by weight, preferably from 10 ppm to 5% by weight.

The aromatic amine compound used in the first process of the invention includes concretely those as is exemplified below.

(1) N,N'-diphenyl-p-phenylenediamine

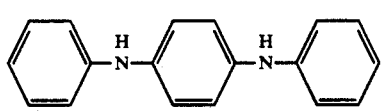

(2) N-phenyl-β-naphthylamine
(trade name: Antage C ®, a product of Kawaguchi Kagaku K.K.)

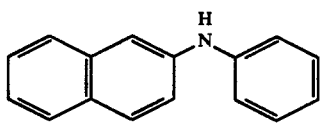

(3) 4,4'-dioctyl-diphenylamine

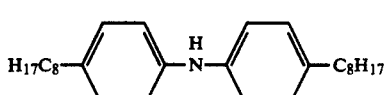

(4) phenothiazine

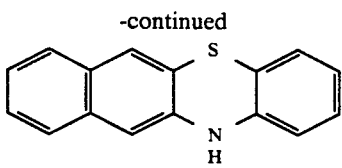

The aromatic amine compounds as exemplifed above are used in an amount, based on the allyl methacrylate used, of from 1 ppm to 20% by weight, preferably from 10 ppm to 5% by weight.

In the first process for the preparation of γ-methacryloxypropylsilane compounds of the invention, an alkylamine compound is used together with at least one of the above-mentioned hindered phenol compound and aromatic amine compound. The alkylamine compound used in the invention may be any of primary, secondary and tertiary amines which may also be silylated.

The alkylamine compound as used herein includes concretely the primary alkylamine compounds such as ethylamine, n-propylamine, isobutylamine, t-butylamine, n-hexylamine, cyclohexylamine, n-octylamine, n-pentylamine, n-heptylamine, n-nonylamine, n-decylamine, n-dodecylamine, n-octadecylamine and benzylamine; the secondary amine compounds such as diethylamine, dipropylamine, dibutylamine, dioctylamine, dihexylamine and dibenzylamine; and the tertiary amine compounds such as triethylamine, tripropylamine, tributylamine, tris(2-ethylhexyl)amine, tri(n-octyl)amine, tribenzylamine, benzyldimethylamine, diethylaminotrimethylsilane {(CH$_3$CH$_2$)$_2$NSi(CH$_3$)$_3$},

diazabicyclo[2.2.2]octane (N⌒N) and quinuclidine (N⌒).

As the alkylamine compounds, there may also be used phenol compounds having an aminoalkylene group as is mentioned later, which are used in the fourth process of the invention.

The alkylamine compounds as mentioned above are used in an amount, based on the platinum catalyst used, of usually more than one equivalent, preferably 1-500 equivalents and especially 10-200 equivalents.

In the second process for the preparation of γ-methacryloxypropylsilane compounds of the invention, an amide compound is used together with at least one compound selected from the group consisting of the above-mentioned hindered phenol compound and aromatic amine compound.

The amide compound used herein includes concretely N,N-dimethylformamide, N,N-dimethylacetamide, N,N-diethylacetamide, N,N-dimethylpropionamide, N-methylacetamide, N-methylformamide, and, in addition, those as is exemplified below.

(1) N-t-butylacetoacetamide

(2) N,N'-bis-3-(3',5'-di-t-butyl-4'-hydroxyphenyl)-propionylhexamethylenediamine
(trade name: Irganox ® 1098, a product of Ciba-Geigy)

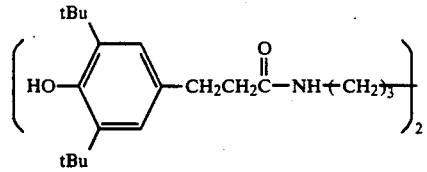

(3) tris[2-(3',5'-di-t-butyl-4'-hydroxyphenylcinnamoyloxy)-ethyl]isocyanurate
(trade name: Irganox ® 3125, a product of Ciba-Geigy)

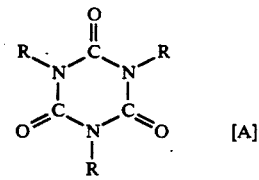

In the above formula [A], R is represented by the following formula.

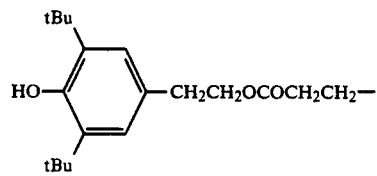

(4) tris(3,5-di-t-butyl-hydroxybenzyl)isocyanurate
(trade name: Irganox ® 3114, a product of Ciba-Geigy)

The compound has the formula [A], provided that R is represented by the following formula.

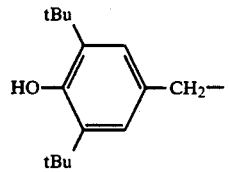

(5) tris(4-t-butyl-2,6-dimethyl-3 hydroxybenzyl)isocyanurate
(trade name: Cyanox ® 1790, a product of ACC Co.)

The compound has the formula [A], provided that R is represented by the following formula.

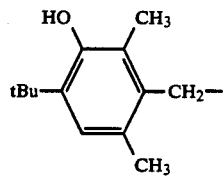

The amide compounds used in the invention may be used either singly or in combination of two or more. In either case, the effective amount of the amide compound used, based on the platinum based catalyst, is more than 1 equivalent, preferably 1-10 equivalents.

In the third process for the preparation of γ-methacryloxypropylsilane compounds of the invention, the reaction of allyl methacrylate with a hydrosilane compound is carried out under the presence of the platinum catalyst, while allowing at least one compound selected from the group consisting of the above-mentioned hindered phenol compound and aromatic amine compound to exist in the reaction system and simultaneously blowing a gas containing molecular oxygen into the reaction mixture containing these compounds as mentioned above.

The gas containing molecular oxygen used in the invention includes a mixed gas with an inert such as nitrogen or argon, or air or oxygen.

The gas containing molecular oxygen preferably contains 0.1-20% of oxygen by volume, especially 0.1-2% of oxygen by volume from the standpoint of safety.

In the third process of the invention, the gas containing molecular oxygen is blown into the reaction mixture at such a rate that the amount of the oxygen molecule, based on 1 mol of the allyl methacrylate used, becomes usually from $1\times10^{-7}$ to $5\times10^{-4}$ mol/min, preferably from $1\times10^{-5}$ to $3\times10^{-4}$ mol/min.

In the fourth process for the preparation of γ-methacryloxypropylsilane compounds of the invention, the above-mentioned hydrosilane compound is allowed to react with allyl methacrylate in the presence of the above-mentioned platinum catalyst, while allowing a phenol compound having an aminoalkylene group to exist in the reaction system. The phenol compound having an aminoalkylene group used in the fourth process of the invention includes those as exemplified below.

(1) 4-(2-aminoethyl)phenol

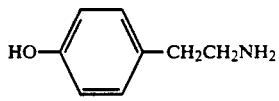

(2) 4-(N,N-dimethylaminomethyl)-2,6-di-t-butylphenol
(trade name: Ethanox ® 703, a product of Ethyl Co.)

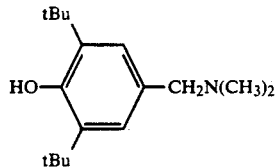

(3) 2-(3,5-di-t-butyl-4-hydroxybenzyl)-2-n-butylmalonic acid-bis(1,2,2,6,6-pentamethyl-4-piperidyl)
(trade name: TINUVIN ® 144, a product of Ciba-Geigy)

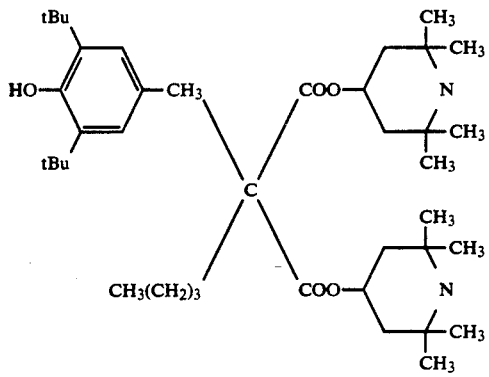

(4) 4-(N,N-dibutylaminomethyl)-2,6-di-t-butylphenol

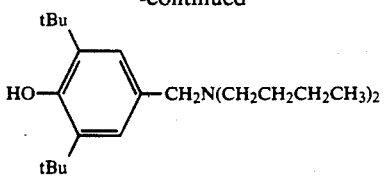

(5) N-methyl-bis(3,5-di-t-butyl-4-hydroxybenzyl)amine

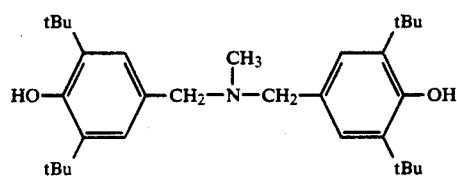

The phenol compound having an aminoalkylene group as exemplified above is used in an amount, based on the platinum catalyst used, of usually more than 1 equivalent, preferably 1-10,000 equivalents and especially 10-1,000 equivalents.

The first to fourth processes for the preparation of γ-methacryloxypropylsilane compounds of the invention by using the starting materials, catalyst and polymerization inhibitor as exemplified hereinbefore may be carried out either in the presence or absence of a reaction solvent.

The reaction solvent used in the processes of the invention includes, for example, aromatic compounds such as benzene, toluene and xylene, aliphatic compounds such as hexane and heptane, and ether compounds such as tetrahydrofuran.

In the processes of the invention, the reaction temperature employed is 40°-130° C., preferably 60°-120° C., and the order of addition of the starting materials, catalyst and polymerization inhibitor is not particularly limited. Furthermore, the processes of the present invention may be carried out in an atmosphere of either oxygen or nitrogen.

In the present invention, allyl methacrylate is allowed to react with the hydrosilane compound as described above to obtain the reaction mixture and then the reaction mixture is subject to purification by distillation to isolate γ-methacryloxypropylsilane compound. In the purification step, a compound selected from the group consisting of the above hindered phenol compound and aromatic amine compound may be added, as a polymerization inhibitor, to the reaction mixture to inhibit the gelation of the reaction mixture more effectively. Further, as the polymerization inhibitor, a compound selected from the group consisting of the hindered phenol compound and the aromatic amide compound may added with alkylamine compound, amide compound or phenol compound having amide alkylene group to the reaction mixture. The polymerization inhibitor used in the purification may be the same as or different from that used in the reaction of the allyl methacrylate with the hydrosilane compound.

The polymerization inhibitor used in purification by distillation is used in a total amount, based on the platinum catalyst, of usually 1-5,000 equivalents and especially 10-1,000 equivalents.

EFFECT OF THE INVENTION

According to the first to fourth processes for the preparation of γ-methacryloxypropylsilane compounds of the present invention, since the reaction of allyl methacrylate with the hydrosilane compound in the presence of the platinum catalyst is carried out in the presence of at least one compound selected from the group consisting of the hindered phenol compound and aromatic amine compound in addition to the alkylamine compound, amide compound, molecular oxygen, or in the presence of the phenol compound having an aminoalkylene group, the gel formation of the reaction mixture during the reaction or during the course of purification by distillation can be effectively avoided, and the γ-methacryloxypropylsilane compounds as desired can be prepared in good yield.

The processes for the preparation of γ-methacryloxypropylsilane compounds of the present invention are illustrated below in more detail with reference to examples, but it should be construed that the invention is in no way limited to those examples. In the examples, percent (%) used is mol% based on the allyl methacrylate used.

EXAMPLE 1

A nitrogen-purged four neck flask equipped with a reflux condenser, a stirrer, a thermometer and a dropping funnel was charged with 126 g of allyl methacrylate, 0.1 ml of a solution of chloroplatinic (IV) acid in isopropanol (corresponding to $10^{-5}$ mol of platinum) and 3 g of tetrakis }methylene-3-(3′,5′-di-t-butyl-4′-hydroxyphenyl)propionate} methane (Irganox ® 1010, a product of Chiba-Geigy) as a radical polymerization inhibitor.

The flask was then charged with 0.1 g of triethylamine, heated at 80° C. by means of an oil bath, and charged dropwise 122 g of trimethoxysilane by means of the dropping funnel over a period of 1 hour. The flask was then kept at 80° C. for 3 hours.

On analysis of the reaction mixture by gas chromatography, it was found that the reaction gave the γ-methacryloxypropyltrimethoxysilane in 88% yield. On analysis of the reaction mixture by GPC, it was confirmed that no polymerizate having a molecular weight of more than 2,000 existed therein.

The reaction mixture was then distilled to isolate the end product.

Results obtained are shown in Table 2.

EXAMPLE 2

The same procedure as described in Example 1 was repeated to carry out the reaction and the isolation of the end product, except that 0.06 g of dibutylamine was used in place of 0.1 g of the triethylamine for the reaction.

Results obtained on analysis of the reaction mixture by gas chromatography and GPC are shown in Table 1, and results obtained on purification of the reaction mixture by distillation are shown in Table 2.

EXAMPLES 3–11

The same procedure as described in Example 1 was repeated to carry out the reaction and the isolation of the end product, except that radical polymerization inhibitors and alkylamine compounds shown in Table 1 were used individually and the reaction was carried out at a temperature as shown in Table 1.

Results obtained on analysis of the reaction mixture by gas chromatography and GPC are shown in Table 1, and results obtained on purification of the reaction mixture by distillation are shown in Table 2.

COMPARATIVE EXAMPLE 1

The same procedure as described in Example 1 was repeated to carry out the reaction except that 0.1 g of the triethylamine was not added to the reaction system.

At the time when about ⅓ of the trimethoxysilane was added dropwise to the flask, the reaction mixture in the flask completely set to gel.

EXAMPLE 12

The same procedure as described in Example 5 was repeated to carry out the reaction except that 164 g of triethoxysilane was used in place of 122 g of the trimethoxysilane.

On analysis of the reaction mixture by gas chromatography, it was found that γ-methacryloxypropyltriethoxysilane was obtained in 85% yield. On analysis of the reaction mixture by GPC, it was confirmed that no polymerizate having a molecular weight of more than 2,000 existed therein.

Subsequently, the reaction mixture was distilled to isolate the end product.

Results obtained are shown in Table 2.

EXAMPLE 13

The same procedure as described in Example 1 was repeated to carry out the reaction except that 148 g of pentamethyldisiloxane was used in place of 122 g of the trimethoxysilane.

On analysis of the reaction mixture by gas chromatography, it was found that γ-methacryloxypropylpentamethyldisiloxane was obtained in 80% yield. On analysis of the reaction mixture by GPC, it was confirmed that no polymerizate having a molecular weight of more than 2,000 existed therein.

Subsequently, the reaction mixture was distilled to isolate the end product.

Results obtained are shown in Table 2.

TABLE 1

| Ex. | Radical polymerization inhibitor | | Alkylamine | | Reaction temperature (°C.) | Yield of product (%) | Amount of polymer formed (%) |
| --- | --- | --- | --- | --- | --- | --- | --- |
| 2 | Irganox ® 1010*1 | (3 g) | (CH3CH2CH2CH2)2NH | (0.06 g) | 80 | 85 | 0.5 |
| 3 | Ethanox ®*2 | (3 g) | (nC8H17)3N | (0.35 g) | 100 | 86 | 0 |
| 4 | Isonox ® 129*3 | (2.8 g) | (nC8H17)NH2 | (0.07 g) | 100 | 87 | 0.2 |
| 5 | BHT*4 | (1.5 g) | 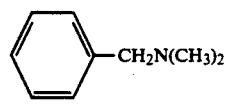 —CH2N(CH3)2 | (0.3 g) | 60 | 84 | 0 |

TABLE 1-continued

| Ex. | Radical polymerization inhibitor | | Alkylamine | | Reaction temperature (°C.) | Yield of product (%) | Amount of polymer formed (%) |
|---|---|---|---|---|---|---|---|
| 6 | Irganox ® 1076*5 | (2.5 g) |  | (0.1 g) | 70 | 87 | 0.1 |
| 7 | N,N'-diphenylphenylene-diamine | (3.0 g) | Et₃N | (0.05 g) | 90 | 81 | 0.3 |
| 8 | — | | Ethanox ® 703*8 | (0.15 g) | 85 | 85 | 0 |
| 9 | Sumilizer ® BBP**6 | (2.5 g) | 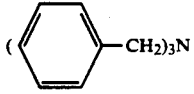 | (0.5 g) | 90 | 83 | 0.2 |
| 10 | Antage DBH*7 | (1.5 g) | Tinuvin ® 144*9 | (0.3 g) | 80 | 82 | 0 |
| 11 | Isonox ® 129**3 | (3.0 g) | Ethanox ® 703*8 | (0.26 g) | 90 | 88 | 0 |

*1Irganox ® 1010 tetrakis{methylene-3-(3',5'-di-t-butyl-4'-hydroxyphenyl)propionate}methane
*2Ethanox ® 702 4,4'-methylenebis(2,5-di-t-butylphenol)
*3Isonox ® 129 2,2'-ethylidene-bis-(4,6-di-t-butyl-phenol)
*4BHT 2,6-di-t-butyl-p-cresol
*5Irganox ® 1076 n-octadecyl-3-(3',5'-di-t-butyl-4'-hydroxyphenyl)propionate
*6Sumilizer ® BBP 2,2'-butylidene-bis-(6-t-butyl-4-methylphenol)
*7Antage DBH 2,5-di-t-butylhydroquinone
*8Ethanox ® 703 4-(N,N-dimethylaminomethyl)-2,6-di-t-butylphenol
*9Tinuvin ® 144 2-(3,5-di-t-butyl-4-hydro-benzyl)-2-n-butylmalonic acid-bis(1,2,2,6,6-penta-methyl-4-piperidyl)

TABLE 2

| Example | Yield of isolated γ-methacryloxypropylsilanes | Distiller bottom polymer (%) |
|---|---|---|
| 1 | 84 | 0 |
| 2 | 80 | 0.8 |
| 3 | 82 | 0.1 |
| 4 | 82 | 0.5 |
| 5 | 81 | 0 |
| 6 | 80 | 0.3 |
| 7 | 76 | 0.7 |
| 8 | 81 | 0 |
| 9 | 79 | 0.2 |
| 10 | 78 | 0 |
| 11 | 80 | 0 |
| 12 | 80 | 0 |
| 13 | 74 | 0.3 |

EXAMPLE 14

The same procedure as described in Example 8 was repeated to carry out the reaction except that 3.7 mg of dichloro(1,5-cyclooctadiene)platinum (II) was used in place of 0.1 ml of a solution of chloroplatinic (IV) acid in isopropanol.

On analysis of the reaction mixture by gas chromatography, it was found that γ-methacryloxypropyl-trimethoxysilane was obtained in 87% yield. On analysis of the reaction mixture by GPC, it was confirmed that no polymerizate having a molecular weight of more than 2,000 exists therein.

Subsequently, the reaction mixture was distilled to isolate the end product in 80% yield without causing gelation thereof.

EXAMPLE 15

The same procedure as described in Example 12 was repeated to carry out the reaction except that a solution of 1,3-divinyltetramethylsiloxane/platinum complex in toluene (corresponding to 1×10⁻⁵ mol of platinum) was used in place of 0.1 ml of the solution of the chloroplatinic (IV) acid in isopropanol.

On analysis of the reaction mixture by gas chromatography, it was found that γ-methacryloxypropyltriethoxysilane was obtained in 85% yield. On analysis of the reaction mixture by GPC, it was confirmed that no polymerizate having a molecular weight of more than 2,000 existed therein.

Subsequently, the reaction mixture was distilled to isolate the end product in 78% yield without causing gelation thereof.

EXAMPLE 16

The same procedure as described in Example 1 was repeated to carry out the reaction except that 100 ml of toluene was used as a reaction solvent.

On analysis of the reaction mixture by gas chromatography, it was found that γ-methacryloxypropyl-trimethoxysilane was obtained in 90% yield, and on analysis of the reaction mixture by GPC, it was confirmed that no polymerizate having a molecular weight of more than 2,000 existed therein.

Subsequently, the reaction mixture was distilled to isolate the end product in 85% yield without causing gelation thereof.

EXAMPLE 17

The same procedure as described in Example 5 was repeated to carry out the reaction except that 150 ml of n-hexane was used as a reaction solvent.

On analysis of the reaction mixture by gas chromatography, it was found that γ-methacryloxypropyl-trimethoxysilane was obtained in 88% yield, and on analysis of the reaction mixture by GPC, it was confirmed that no polymerizate having a molecular weight of more than 2,000 existed therein.

Subsequently, the reaction mixture was distilled to isolate the end product in 83% yield without causing gelation thereof.

COMPARATIVE EXAMPLE 2

The same procedure as described in Example 16 was repeated to carry out the reaction except that 0.1 g of the triethylamine was not added to the reaction system.

On analysis of the reaction mixture by gas chromatography, it was found that γ-methacryloxypropyltrimethoxysilane was obtained in 65% yield.

Subsequently, the reaction mixture was distilled to isolate the end product merely in 40% yield, bringing about a gel formed in the distiller bottom.

EXAMPLE 18

The same procedure as described in Example 1 was repeated to carry out the reaction except that 300.6 g of pentamethylcyclopentasiloxane as shown below was used in place of 122 g of the trimethoxysilane.

On analysis of the reaction mixture by gas chromatography, it was found that γ-methacryloxypropylpentamethylcyclopentasiloxane was obtained in 64% yield. On analysis of the reaction mixture by GPC, it was confirmed that no polymerizate having a molecular weight of more than 2,000 existed therein.

EXAMPLE 19

The same procedure as described in Example 1 was repeated to carry out the reaction except that in place of 122 g of the trimethoxysilane, there was used 500 g of polymethylhydrogensiloxane (100 cSt: content of SiH group represented by the following formula.

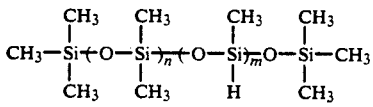

On analysis of the reaction mixture by gas chromatography, it was found that the conversion of allyl methacrylate is 85%, and no polymerizate was formed.

EXAMPLE 20

The same procedure as described in Example 3 was repeated to carry out the reaction except that the amount of the tri-n-octylamine used was changed from 0.35 g to 3.5 mg.

On analysis of the reaction mixture by gas chromatography, it was found that γ-methacryloxypropyltrimethoxysilane was obtained in 83% yield. On analysis of the reaction mixture by GPC, it was confirmed that the amount of a polymerizate having a molecular weight of more than 2,000 as formed was 2.3% based on the starting materials.

Subsequently, the reaction mixture was distilled to isolate the end product in 75% yield, and no gelation took place though the amount of the polymerizate increased to 5%.

EXAMPLE 21

0.7 g of tri n-octylamine was added, to the reaction mixture obtained in Example 20 and the resulting mixture was distilled, whereby γ-methacryloxypropyltrimethoxysilane was isolated in 78% yield, and no increase of the polymerizate was observed.

EXAMPLE 22

The same procedure as described in Example 8 was repeated to carry out the reaction except that 0.14 g of 4-(2-aminoethyl)phenol was used in place of 0.15 g of Ethanox ® 703.

On analysis of the reaction mixture by gas chromatography, it was found that γ-methacryloxypropyltrimethoxysilane was obtained in 82% yield.

Subsequently, the reaction mixture was distilled to isolate the end product in 75% yield, and no gelation took place.

EXAMPLE 23

A nitrogen-purged four neck flask equipped with a reflux condenser, a stirrer, a thermometer and a dropping funnel was charged with 126 g of allyl methacrylate, 0.1 ml of a solution of chloroplatinic (IV) acid in isopropanol (corresponding to $10^{-5}$ mol of platinum) and 2.8 g of 2,2'-ethylidenebis-(4,6-t-butylphenol) (trade name: Isonox ® 129, a product of Schenectady Co.) as a radical polymerization inhibitor.

Subsequently, the flask was charged with 17.4 mg of N,N-dimethylacetamide, heated at 80° C. by means of an oil bath, and then charged dropwise with 122 g of trimethoxysilane by means of the dropping funnel over a period of 1 hour. The flask was then kept at 80° C. for 5 hours.

On analysis of the reaction mixture by gas chromatography, it was found that γ-methacryloxypropyltrimethoxysilane was obtained in 83% yield. On analysis of the reaction mixture by GPC, it was confirmed that no polymerizate having a molecular weight of more than 2,000 existed therein.

Subsequently, the reaction mixture was distilled to isolate the end product, whereby no gelation took place.

Results obtained are shown in Table 4.

EXAMPLE 24

The same procedure as described in Example 23 was repeated to carry out the reaction and isolate the end product except that 21.9 mg of N-methylacetamide was used in place of 17.4 mg of the N,N-dimethylacetamide.

Results obtained on analysis of the reaction mixture by gas chromatography and by GPC are shown in Table 3, and results obtained on purification of the reaction mixture by distillation are shown in Table 4.

EXAMPLES 25-32

The same procedure as described in Example 23 was repeated to carry out the reaction and isolate the end product except that radical polymerization inhibitors, hydrosilane compounds and amide compounds as shown in Table 3 were used individually, and the reaction was carried out at each temperature as shown in Table 3.

Results obtained on analysis of the reaction mixture by gas chromatography and by GPC are shown in Table 3, and results obtained on purification of the reaction mixture by distillation are shown in Table 4.

TABLE 3

| Ex. | Radical polymerization inhibitor | | Amide compound | | Hydrosilane compound | | Reaction temperature (°C.) | Yield of product (%) | Amount of polymer formed (%) |
|---|---|---|---|---|---|---|---|---|---|
| 24 | Irganox ® 1010*[1] | (3.2 g) | N,N-dimethylformamide | (7.3 mg) | HSi(OMe)$_3$ | (122 g) | 80 | 85 | 0.1 |
| 25 | Ethanox ® 702*[2] | (3.0 g) | N-methylformamide | (17.7 mg) | HSi(OMe)$_3$ | (122 g) | 90 | 86 | 0 |
| 26 | BHT*[3] | (1.4 g) | N,N-diethylacetamide | (23 mg) | HSi(OMe)$_2$Me | (106 g) | 75 | 83 | 0.2 |
| 27 | Sumilizer ® BBP*[4] | (2.8 g) | Irganox ® 1098*[7] | (0.25 g) | HSi(OMe)Me$_2$ | (90 g) | 85 | 84 | 0.1 |
| 28 | Antage ® DBH*[5] | (1.7 g) | Irganox ® 3114*[8] | (78 mg) | HSi(OEt)$_3$ | (164 g) | 100 | 83 | 0 |
| 29 | Irganox ® 1076*[6] | (2.5 g) | Cyanox ® 1790*[9] | (0.14 g) | HSi(OMe)$_3$ | (122 g) | 90 | 85 | 0 |
| 30 | N,N-diphenylphenylenediamine | (3.0 g) | Irganox ® 3125*[10] | (0.10 g) | HSiEt$_3$ | (116 g) | 100 | 86 | 0.1 |
| 31 | Ethanox ® 702*[2] | (1.5 g) | N-methylformamide | (17.7 mg) | H(CH$_3$)$_2$SiOSi(CH$_3$)$_2$H | (148 g) | 100 | 84 | 0.1 |
| 32 | Ethanox ® 702*[2] | (2.0 g) | N-methylacetamide | (14.6 mg) | Pentamethylcyclopentasiloxane | (300 g) | 90 | 75 | 0 |

*[1]Irganox ® 1010 tetrakis{methylene-3-(3',5'-di-t-butyl-4'-hydroxyphenyl)propionate}methane
*[2]Ethanox ® 702 4,4'-methylenebis(2,6-di-t-butylphenol)
*[3]BHT 2,6-di-t-butyl-p-cresol
*[4]Sumilizer ® BBP 2,2'-butylidene-bis(6-t-butyl-4-methylphenol)
*[5]Antage ® DBH 2,5-di-t-butylhydroquinone
*[6]Irganox ® 1076 n-octadecyl-3-(3',5'-di-t-butyl-4'-hydroxyphenyl)propionate
*[7]Irganox ® 1098 N,N'-bis-3-(3',5'-di-t-butyl-4'-hydroxyphenyl)propionylhexamethylenediamine
*[8]Irganox ® 3114 tris(3,5-di-t-butyl-4-hydroxybenzyl)isocyanurate
*[9]Cyanox ® 1790 tris(4-t-butyl-2,6-dimethyl-3-hydroxybenzyl)isocyanurate
*[10]Irganox ® 3125 tris[2-(3',5'-di-t-butyl-4'-hydroxyphenylcinnamoyloxy)ethyl]isocyanurate

TABLE 4

| Example | Yield of γ-methacryloxypropyl-silanes isolated (%) | Distiller bottom polymer (%) |
|---|---|---|
| 23 | 77 | 2 |
| 24 | 79 | 0.8 |
| 25 | 80 | 0.1 |
| 26 | 78 | 0.5 |
| 27 | 79 | 0.1 |
| 28 | 76 | 0.2 |
| 29 | 80 | 0.1 |
| 30 | 80 | 0.1 |
| 31 | 77 | 0.3 |
| 32 | 68 | 0.1 |

COMPARATIVE EXAMPLE 3

The same procedure as described in Example 23 was repeated to carry out the reaction except that 17.4 mg of the N,N-dimethylacetamide was not added to the reaction system.

At the time when about ⅓ of the trimethoxysilane was added dropwise to the reaction system, the reaction mixture in the flask completely set to gel.

EXAMPLE 33

The same procedure as described in Example 23 was repeated to carry out the reaction except that 0.2 ml of a solution of 1,3-divinyltetramethylsiloxane/platinum complex in toluene (corresponding to 10$^{-5}$ mol of platinum) was used in place of 0.1 ml of the solution of chloroplatinic (IV) acid in isopropanol.

On analysis of the reaction mixture by gas chromatography, it was found that γ-methacryloxypropyl-trimethoxysilane was obtained in 84% yield. On analysis of the reaction mixture by GPC, it was confirmed that no polymerizate having a molecular weight of more than 2,000 existed therein.

Subsequently, the reaction mixture was distilled to isolate the end product in 79% yield without causing gelation thereof.

EXAMPLE 34

The same procedure as described in Example 24 was repeated to carry out the reaction except that 3.7 mg of dichloro(1,5-cyclooctadiene)platinum (II) was used in place of 0.1 ml of the solution of chloroplatinic (IV) acid in isopropanol.

On analysis of the reaction mixture by gas chromatography, it found that γ-methacryloxypropyltrimethoxysilane was obtained in 86% yield. On analysis of the reaction mixture by GPC, it was confirmed that no polymerizate having a molecular weight of more than 2,000 existed therein.

Subsequently, the reaction mixture was distilled to isolate the end product in 80% yield without causing gelation thereof.

EXAMPLE 35

The same procedure as described in Example 23 was repeated to carry out the reaction except that 500 g of polymethylhydrogensiloxane (100 cSt: the content of SiH group 10%) represented by the following formula.

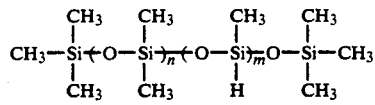

On analysis of the reaction mixture by gas chromatography, it was found that the conversion of allyl methacrylate was 90%. On analysis of the reaction mixture by GPC, it was confirmed that no polymerizate having a molecular weight of more than 2,000 existed therein.

EXAMPLE 36

The same procedure as described in Example 23 was repeated except that 100 ml of toluene was used as a reaction solvent.

On analysis of the reaction mixture by gas chromatography, it was found that γ-methacryloxypropyltrimethoxysilane was obtained in 87% yield. On analysis of the reaction mixture by GPC, it was confirmed that no polymerizate having a molecular weight of more than 2,000 existed therein.

Subsequently, the reaction mixture was distilled to isolate the end product in 81% yield without causing gelation thereof, and the polymer in the distillation residue was 1.5%.

EXAMPLE 37

The same procedure as described in Example 23 was repeated to carry out the reaction except that 100 ml of n-hexane was used as a reaction solvent.

On analysis of the reaction mixture by gas chromatography, it was found that γ-methacryloxypropyltrimethoxysilane was obtained in 88% yield.

On analysis of the reaction mixture by GPC, it was confirmed that no polymerizate having a molecular weight of more than 2,000 existed therein.

Subsequently, the reaction mixture was distilled to isolate the end product in 81% yield without causing gelation thereof, and the polymer in the distillation residue was 1.0%.

COMPARATIVE EXAMPLE 4

The same procedure as described in Example 36 was repeated to carry out the reaction except that 17.4 mg of the N,N-dimethylacetamide was not added to the reaction system.

On analysis of the reaction mixture by gas chromatograph, it became a viscous solution, though no gelation thereof took place, and it was found that γ-methacryloxypropyltrimethoxysilane was obtained in 65% yield.

Subsequently, the reaction mixture was distilled to isolate the end product merely in 40% yield, forming a gel in the distiller bottom.

EXAMPLE 38

To the reaction mixture obtained in Example 23, 87.1 mg of N,N-dimethylacetamide was added, and the resulting mixture was distilled to isolate the end product, whereby γ-methacryloxypropyltrimethoxysilane was isolated in 79% yield without causing gelation thereof, and the polymer in the distillation residue was 0.4%.

EXAMPLE 39

The same four peck flask as used in Example 23 but having a gas blowing head was charged with 126 g of allyl methacylrate, 0.1 ml of a solution of chloroplatinic (IV) acid in isopropanol (corresponding to $10^{-5}$ mol of platinum) and 1.0 g of 2,6-di-t-butyl-p-cresol (BHT) as a radical polymerization inhibitor, followed by heating at 80° C. on an oil bath.

Subsequently, into the reaction liquid was blown through the gas blowing head with $O_2/N_2$ gas containing 2% of oxygen by volume at a rate of 300 ml/min based on 1 mol of the allyl methacrylate. While continuing the blowing of the gas, 122 g of trimethoxysilane was added dropwise by means of the dropping funnel to the reaction liquid over a period of 1 hour, and the heating was continued at 80° C. for 5 hours. The gas blowing was further continued after the completion of the addition of the trimethoxysilane.

On analysis of the reaction mixture by gas chromatography, it was found that γ-methacryloxypropyltrimethoxysilane was formed in 83% yield. On analysis of the reaction mixture by GPC, it was confirmed that a polymerizate having a molecular weight of more than 2,000 in the reaction mixture was less than 0.1%.

EXAMPLES 40–43

The same procedure as described in Example 39 was repeated to carry out the reaction and isolate the end product except that the reaction was carried out using radical polymerization inhibitors as shown in Table 5.

Results obtained on analysis of the reaction mixture by gas chromatography and by GPC are shown in Table 5.

COMPARATIVE EXAMPLE 5

The same procedure as described in Example 39 was repeated to carry out the reaction except that $N_2$ gas was used as the blowing gas.

In the course of the reaction, the reaction mixture present in the flask set to gel.

Results obtained are shown in Table 5.

COMPARATIVE EXAMPLE 6

The same procedure as described in Comparative Example 5 was repeated to carry out the reaction except that 3 g of 4,4'-methylene-bis(2,3-di t-butylphenol) (trade name: Ethanox ® 702, a product of Ethyl Co.) was used as a radical polymerization inhibitor.

Results obtained on analysis of the reaction mixture by gas chromatography and by GPC are shown in Table 5.

COMPARATIVE EXAMPLE 7

The same procedure as described in Example 39 was repeated to carry out the reaction except that no radical polymerization inhibitor was used.

Results obtained on analysis of the reaction mixture by gas chromatography and by GPC are shown in Table 5.

TABLE 5

| | Radical polymerization inhibitor | | Blowing gas (vol %) | Flow rate based on 1 mol of allyl methacrylate (ml/min) | Hydrosilane compound | Reaction temperature (°C.) | Yield of product (%) | Amount of polymer formed (%) |
|---|---|---|---|---|---|---|---|---|
| Ex. | | | | | | | | |
| 40 | Ethanox ® 702*[1] | (3 g) | 2% $O_2/N_2$ | 300 | $HSi(OMe)_3$ | 80 | 85 | <0.1 |
| 41 | Irganox ® 1010*[2] | (3 g) | 2% $O_2/N_2$ | 300 | $HSi(OMe)_3$ | 80 | 85 | <0.1 |
| 42 | N,N-diphenylethylenediamine | (1 g) | 2% $O_2/N_2$ | 300 | $HSi(OMe)_3$ | 80 | 82 | <0.1 |
| 43 | Antage ® DBH*[3] | (1 g) | 2% $O_2/N_2$ | 300 | $HSi(OMe)_3$ | 80 | 81 | <0.1 |
| Compar. Ex. | | | | | | | | |
| 5 | BHT*[4] | (1 g) | $N_2$ | 300 | $HSi(OMe)_3$ | 80 | Gelled | — |
| 6 | Ethanox ® 702*[1] | (3 g) | $N_2$ | 300 | $HSi(OMe)_3$ | 80 | Gelled | — |

TABLE 5-continued

| Radical polymerization inhibitor | Blowing gas (vol %) | Flow rate based on 1 mol of allyl methacrylate (ml/min) | Hydrosilane compound | Reaction temperature (°C.) | Yield of product (%) | Amount of polymer formed (%) |
| --- | --- | --- | --- | --- | --- | --- |
| 7 | 2% O$_2$/N$_2$ | 300 | HSi(OMe)$_3$ | 80 | 32 | 14 |

*[1]Ethanox ® 702 4,4'-methylenebis(2,6-di-t-butylphenol)
*[2]Irganox ® 1010 tetrakis{methylene-3-(3',5'-di-t-butyl-4'-hydroxyphenyl)propionate}methane
*[3]Antage ® DBH 2,5-di-t-butylhydroquinone
*[4]BHT 2,6-di-t-butyl-p-cresol

EXAMPLE 44

The same procedure as described in Example 39 was repeated to carry out the reaction except that O$_2$/N$_2$ gas containing 20% of oxygen by volume was used as the blowing gas.

On analysis of the reaction mixture by gas chromatography, it was found that γ-methacryloxypropyltrimethoxysilane was obtained in 84% yield. On analysis of the reaction mixture by GPC, it was confirmed that a polymerizate having a molecular weight of more than 2,000 therein was less than 0.1%.

EXAMPLE 45

The same procedure as described in Example 39 was repeated except that O$_2$/N$_2$ gas containing 0.2% of oxygen by volume was used as the blowing gas.

On analysis of the reaction mixture by gas chromatography, it was found that γ-methacryloxypropyltrimethoxysilane was obtained in 85% yield. On analysis of the reaction mixture by GPC, it was confirmed that a polymerizate having a molecular weight of more than 2,000 therein was less than 0.1%.

EXAMPLE 46

The same procedure as described in Example 39 was repeated to carry out the reaction except that 0.26 ml of a solution of 1,3-divinyltetramethylsiloxane/platinum complex in toluene (corresponding to $10^{-5}$ mol of platinum) was used in place of 0.1 ml of the solution of chloroplatinic (IV) acid in isopropanol.

On analysis of the reaction mixture by gas chromatography, it was found that γ-methacryloxypropyltrimethoxysilane was obtained in 85% yield. On analysis of the reaction mixture by GPC, it was confirmed that a polymerizate having a molecular weight of more than 2,000 therein was less than 0.1%.

EXAMPLE 47

The same procedure as described in Example 41 was repeated to carry out the reaction except that 3.7 mg of dichloro(1,5-cyclooctadiene)platinum (II) was used in place of 0.1 ml of the solution of chloroplatinic (IV) acid in isopropanol.

On analysis of the reaction mixture by gas chromatography, it was found that γ-methacryloxypropyltrimethoxysilane was obtained in 82% yield. On analysis of the reaction mixture by GPC, it was confirmed that a polymerizate having a molecular weight of more than 2,000 therein was less than 0.1%.

EXAMPLE 48

The same procedure as described in Example 39 was repeated except that 500 g of polymethylhydrogensiloxane (100 cSt: the content of SiH group 10%) was used as the hydrosilane compound.

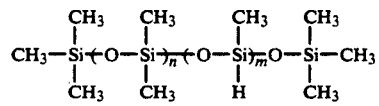

On analysis of the reaction mixture by gas chromatography, it was found that the conversion of the allyl methacrylate was 93%. On analysis of the reaction mixture by GPC, it was confirmed that no polymerizate of a high molecular weight existed therein.

EXAMPLE 49

The same procedure as described in Example 39 was repeated except that 100 ml of toluene was used as a reaction solvent.

On analysis of the reaction mixture by gas chromatography, it was found that γ-methacryloxypropyltrimethoxysilane is obtained in 84% yield.

COMPARATIVE EXAMPLE 8

The same procedure as described in Example 39 was repeated to carry out the reaction except that prior to charging the flask with the starting materials, platinum catalyst and radical polymerization inhibitor, the flask was purged with dry air and no gas-blowing was carried out.

In the course of the reaction, the reaction mixture became viscous and set to gel.

What is claimed is:

1. A process for the preparation of γ-methacryloxypropylsilane compounds which comprises carrying out the reaction of allyl methacrylate with a hydrosilane compound in the presence of a platinum catalyst, while allowing at least one of a hindered phenol compound and an aromatic amine compound to coexist in the reaction system with an alkylamine compound.

2. The process for the preparation of γ-methacryloxypropylsilane compounds as claimed in claim 1 wherein the alkylamine compound is a phenol compound having an aminoalkylene group.

3. A process for the preparation of γ-methacryloxypropylsilane compounds which comprises carrying out the reaction of allyl methacrylate with a hydrosilane compound in the presence of a platinum catalyst to obtain a reaction product, while allowing at least one of a hindered phenol compound and an aromatic amine compound to coexist in the reaction system with an amide compound.

4. The process for the preparation of γ-methacryloxypropylsilane compounds as claimed in claim 3 wherein the amide compound is added further to the reaction mixture obtained, and the resulting reaction mixture is purified by distillation.

5. A process for the preparation of γ-methacryloxypropylsilane compounds which comprises carrying out the reaction of allyl methacrylate with a hydrosilane compound in the presence of a platinum catalyst, while allowing at least one of a hindered phenol compound and an aromatic amine compound to exist in the reaction system and blowing a gas containing molecular oxygen into the reaction solution.

6. A process for the preparation of γ-methacryloxypropylsilane compounds which comprises carrying out the reaction of allyl methacrylate with a hydrosilane compound in the presence of a platinum catalyst, while allowing a phenol compound having an aminoalkylene group to exist in the reaction system.

* * * * *